(12) United States Patent
Fitzgerald et al.

(10) Patent No.: US 7,797,172 B2
(45) Date of Patent: Sep. 14, 2010

(54) HEALTHCARE FINANCIAL DATA AND CLINICAL INFORMATION PROCESSING SYSTEM

(75) Inventors: David Fitzgerald, West Grove, PA (US); Brian Lucas, Springfield, PA (US); Greg Long, Conshohocken, PA (US); David Hiebert Klassen, Sr., Paoli, PA (US); John Hunter, North Wales, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 2836 days.

(21) Appl. No.: 10/253,223

(22) Filed: Sep. 24, 2002

(65) Prior Publication Data

US 2003/0195771 A1 Oct. 16, 2003

Related U.S. Application Data

(60) Provisional application No. 60/373,073, filed on Apr. 16, 2002.

(51) Int. Cl.
 *G06Q 40/00* (2006.01)
(52) U.S. Cl. .......................................................... 705/4
(58) Field of Classification Search .................. 705/2–4
 See application file for complete search history.

(56) References Cited

U.S. PATENT DOCUMENTS

| | | | |
|---|---|---|---|
| 4,491,725 A | 1/1985 | Pritchard | |
| 4,667,292 A | 5/1987 | Mohlenbrock et al. | |
| 4,852,000 A | 7/1989 | Webb et al. | |
| 4,857,716 A | 8/1989 | Gombrich et al. | |
| 4,858,121 A | 8/1989 | Barber et al. | |
| 5,018,067 A | 5/1991 | Mohlenbrock et al. | |
| 5,077,666 A | 12/1991 | Brimm et al. | |
| 5,121,945 A | 6/1992 | Thomson et al. | |
| 5,191,522 A | 3/1993 | Bosco et al. | |
| 5,253,164 A * | 10/1993 | Holloway et al. | 705/2 |
| 5,301,105 A | 4/1994 | Cummings, Jr. | 705/2 |
| 5,307,262 A | 4/1994 | Ertel | |
| 5,325,293 A | 6/1994 | Dorne | |
| 5,359,509 A * | 10/1994 | Little et al. | 705/2 |

(Continued)

FOREIGN PATENT DOCUMENTS

JP 11161704 A 6/1999

*Primary Examiner*—Gerald J. O'Connor
*Assistant Examiner*—Sheetal R Rangrej

(57) ABSTRACT

A patient claim data processing system responds to and initiates clinical events and attains early accurate claim data during a patient healthcare encounter cycle to support prompt claim data validation and editing both for individual claim elements and for a completed claim to improve claim accuracy prior to claim submission to a payer. The system submits accurate claims to payers and receives remittance advice from payers and applies rules to the advice. A system processes financial data related to provision of healthcare to a patient in response to clinical events. The system includes an interface processor for receiving a message identifying an event and a related change in healthcare data concerning a patient and also includes a source of rules for determining characteristics associated with reimbursement for provision of an individual service to a patient. A rules processor initiates application of a rule derived from the rules source to process financial data concerning provision of the individual service to the patient in response to receiving the message identifying the event. A result processor initiates an action in response to a result derived by the application of the rule to process the financial data. The rules processor also validates the financial data complies with the rule.

11 Claims, 15 Drawing Sheets

U.S. PATENT DOCUMENTS

| | | | |
|---|---|---|---|
| 5,517,405 A | 5/1996 | McAndrew et al. | 364/401 |
| 5,550,734 A | 8/1996 | Tarter et al. | |
| 5,557,514 A | 9/1996 | Seare et al. | |
| 5,704,371 A | 1/1998 | Shepard | |
| 5,752,234 A | 5/1998 | Withers | |
| 5,772,585 A | 6/1998 | Lavin et al. | |
| 5,790,674 A | 8/1998 | Houvener et al. | |
| 5,819,228 A | 10/1998 | Spiro | |
| 5,835,897 A | 11/1998 | Dang | |
| 5,867,821 A | 2/1999 | Ballantyne et al. | |
| 5,915,241 A * | 6/1999 | Giannini | 705/2 |
| 5,924,074 A | 7/1999 | Evans | 705/3 |
| 5,933,809 A | 8/1999 | Hunt et al. | |
| 5,950,169 A * | 9/1999 | Borghesi et al. | 705/4 |
| 5,956,689 A | 9/1999 | Everhart, III | |
| 5,974,389 A | 10/1999 | Clark et al. | |
| 5,991,733 A | 11/1999 | Aleia et al. | 705/8 |
| 6,182,070 B1 | 1/2001 | Megiddo et al. | |
| 6,189,005 B1 | 2/2001 | Chakrabarti et al. | |
| 6,263,330 B1 | 7/2001 | Bessette | 707/4 |
| 6,282,531 B1 | 8/2001 | Haughton et al. | 706/50 |
| 6,317,783 B1 | 11/2001 | Freishtat et al. | |
| 6,336,139 B1 | 1/2002 | Feridun et al. | |
| 6,341,265 B1 * | 1/2002 | Provost et al. | 705/4 |
| 6,343,271 B1 | 1/2002 | Peterson et al. | 705/4 |
| 6,345,288 B1 | 2/2002 | Reed et al. | |
| 2001/0034618 A1 | 10/2001 | Kessler et al. | |
| 2001/0037224 A1 | 11/2001 | Eldridge et al. | |
| 2001/0054155 A1 | 12/2001 | Hagan et al. | |
| 2002/0004727 A1 | 1/2002 | Knaus et al. | |
| 2002/0010597 A1 | 1/2002 | Mayer et al. | |
| 2002/0019754 A1 | 2/2002 | Peterson et al. | 705/4 |
| 2002/0032583 A1 | 3/2002 | Joao | 705/2 |
| 2002/0032584 A1 | 3/2002 | Doctor et al. | |
| 2002/0120473 A1 | 8/2002 | Wiggins | |
| 2002/0133503 A1 | 9/2002 | Amar et al. | |
| 2002/0147867 A1 | 10/2002 | Satlow | |
| 2002/0198741 A1 | 12/2002 | Randazzo | |
| 2003/0014280 A1 | 1/2003 | Jilinskaia et al. | |
| 2003/0018496 A1 | 1/2003 | Hambright et al. | |
| 2003/0050804 A1 | 3/2003 | Hendershot | |
| 2003/0055679 A1 | 3/2003 | Soll et al. | 705/2 |
| 2003/0069760 A1 | 4/2003 | Gelber | 705/4 |
| 2003/0083906 A1 | 5/2003 | Howell et al. | |
| 2003/0191665 A1 | 10/2003 | Fitzgerald et al. | |
| 2003/0191667 A1 | 10/2003 | Fitzgerald et al. | |
| 2003/0191669 A1 | 10/2003 | Fitzgerald et al. | |
| 2004/0078228 A1 | 4/2004 | Fitzgerald et al. | |

* cited by examiner

```
session_a-RUMBA Mainframe Display                                                    _ □ ×
File Edit View Connection Transfer Options Tools Help
[icons...]                                                                              420
06/14/02  12:28PM              EGL  SINGLE  GENERAL  HOSPITAL         UB92   REV-CODES  SECTION
PAT#   2969      NAME:  MORETHANTWENTYSIX, TES AREA:    ACLMED     SEX/DOB:  M   01/11/1967
     Entire-List ======= UB92 CLAIM MANAGER  =========================    CLAIMID# 10129608 ========

SEQ#  I/D   REVCD        TYPE   SVC DATE    UNITS/DAYS    RATE / PROC      TOTL CHARGES    NON - CVD CHRG
 1          540           A     04/29/02         2         A0425
            AMBULANCE
 2          250           C     04/29/02         1         27301             2000.00
            PHARMACY                                       DRAIN THIGH / KNEE LESION
 3          250           C     04/29/02         1         27305
            PHARMACY                                       INCISE THIGH TENDON & FASCIA

** ERROR:   Revenue Code #1 invalid < 540 >
** ERROR:   Acom Rate/Ancil Proc Cd #1 not in format n.nn- < A0425 >
   WARNING: Revenue Code #1 present < 540 >
   WARNING: Accomodatn/Ancillary Ind #1 present < A >
   WARNING: Acom Days/Ancil Units #1 present < 2 >
&AMBULANC    &MOTORVEH    &ALCOHOL      &PAYOR       &VOCS         &PACEMAKE     G10306A
&PATDATA     &EXIT        &CANCEL       &ERRLIST     &MENU         &MEDICAL      G50312A
&APCDTL      &CLEAR       &ALLMSG       &PREVAREA                                G20306A
                                                        ACTION ==>                G20303A
                                                                                  G20318A
Ready                    Running          APL NUMFLD SNA1@120 OVR CAP NUM W  9,13  12:32:28 PM
```

402 — SEQ# 1 row
404 — SEQ# 2 row
406 — SEQ# 3 row

FIG. 4

| | RULE |
|---|---|
| 1. | CALCULATE EXPECTED REIMBURSEMENT FOR THE RESPONSIBLE PARTY. |
| 2. | CHECK FOR EFFECTIVE BENEFIT PERIOD. |
| 3. | CHECK THAT THE HEALTH PROVIDER ORGANIZATION OR HEALTH PROFESSIONAL IS REIMBURSED ACCORDING TO THE TERMS OF THE CONTRACT. |
| 4. | QUALIFY CHARGES FOR CONTRACT AND BENEFIT PACKAGES, TERMS AND NON-COVERED GROUPS. |
| 5. | DETERMINE IF CHARGE IS COVERED OR NOT. |
| 6. | SUPPORT RECURRING OUTPATIENTS |
| 7. | SUPPORT MULTIPLE DISCOUNT MODIFIER CODE ADJUSTMENTS |
| 8. | USE ENCOUNTER SPECIFIC BENEFITS. |
| 9. | LINK PRE-ADMISSION TESTING ENCOUNTERS TO SURGICAL ENCOUNTERS |
| 10. | LINK SAME DAY SURGERY ENCOUNTERS TO INPATIENT ENCOUNTERS |
| 11. | LINK MOTHERS WITH NEWBORNS |
| 12. | MOTHERS LINKED WITH NEWBORNS |
| 13. | LINK ENCOUNTERS WHEN OUTPATIENT CHARGES ARE PERFORMED ON THE SAME DAY AS THE START OF AN INPATIENT ENCOUNTER |

FIG. 5

| | RULE |
|---|---|
| 521 — 1. | DROP AN INPATIENT INSURANCE CLAIM 5 DAYS AFTER DISCHARGE. |
| 522 — 2. | 10 DAYS LATER, ISSUE A CLAIM STATUS INQUIRY TO ENSURE THAT THE CLAIM IS BEING PROCESSED. |
| 523 — 3. | IF NO PAYMENT IS RECEIVED 30 DAYS AFTER DISCHARGE, CREATE A FOLLOW UP WORKLIST ENTRY. |
| 524 — 4. | IF NO PAYMENT IS RECEIVED 15 DAYS AFTER THAT, ISSUE A REBILL. |
| 525 — 5. | IF PAYMENT IS STILL NOT RECEIVED, TRANSFER THE BALANCE TO THE NEXT PAYER 30 DAYS LATER. BEGIN A 30 DAY STATEMENT CYCLE WHEN INITIAL GUARANTOR RESPONSIBILITY IS ASSIGNED. |
| 526 — 6. | CREATE TWO STATEMENTS, INCREASING THE DUNNING MESSAGE LEVEL ON THE SECOND ONE |
| 527 — 7. | IF NO PAYMENT IS RECEIVED AFTER THE SECOND STATEMENT, CREATE A FOLLOW UP WORKLIST ENTRY. |
| 528 — 8. | CONTINUE GENERATING STATEMENTS ON THE 30 DAY CYCLE WITH INCREASING DUNNING LEVELS. |
| 529 — 9. | IF PAYMENT IS NOT RECEIVED IN 90 DAYS CREATE A FIRST PARTY COLLECTION LETTER. |
| 530 — 10. | IF PAYMENT IS NOT RECEIVED IN 120 DAYS, TRANSFER TO A COLLECTION AGENCY. |

FIG. 6

Patient record

| | | | | | |
|---|---|---|---|---|---|
| PATIENT RECORD, | | | | | |
| 800 — PACKET_ID | CHAR(5), | /* claim packet number | | | 0 */ |
| 802 — SECTION_ID | CHAR(8), | /* section id - "PATIENT" | | | 5 */ |
| 804 — SEQ_NUM | PIC'(4)9', | /* record sequence number | | | 13 */ |
| 806 — PAT_LAST_NM | CHAR(20), | /* PATIENT LAST NAME | 20 - 4 | | 17 */ |
| 808 — PAT_FIRST_NM | CHAR(12), | /* PATIENT FIRST NAME | 20 - 5 | | 37 */ |
| 810 — PAT_MIDDL_I | CHAR(1), | /* PATIENT MIDDLE INITIAL | 20 - 6 | | 49 */ |
| PAT_ADDR_1 | CHAR(25), | /* PATIENT ADDRESS 1 | 20 - 12 | | 50 */ |
| PAT_ADDR_2 | CHAR(25), | /* PATIENT ADDRESS 2 | 20 - 13 | | 75 */ |
| PAT_CITY | CHAR(15), | /* PATIENT CITY | 20 - 14 | | 100 */ |
| PAT_STATE | CHAR(2), | /* PATIENT STATE | 20 - 15 | | 115 */ |
| PAT_ZIP | CHAR(9), | /* PATIENT ZIP | 20 - 16 | | 117 */ |
| PAT_COUNTRY_CD | CHAR(2), | /* PATIENT COUNTRY CODE | N404 | | 126 */ |
| PAT_COUNTY | CHAR(2), | /* PATIENT COUNTY CODE | 25 - 22 | | 128 */ |
| PAT_PHONE | CHAR(14), | /* phone# aaaxxxxxxx Ext4 | 26 - 4 | | 130 */ |
| PAT_SEX | CHAR(1), | /* PATIENT SEX | 20 - 7 | | 144 */ |
| PAT_DOB | CHAR(8), | /* PATIENT BIRTH DATE | 20 - 8 | | 145 */ |
| PAT_SOC_SEC | CHAR(9), | /* PATIENT SOCIAL SEC# | 86 - 8 | | 153 */ |
| PAT_MARTL | CHAR(1), | /* PATIENT MARITAL STS | 20 - 9 | | 162 */ |
| PAT_RACE | CHAR(2), | /* PATIENT RACE | 25 - 13 | | 163 */ |
| PAT_ETHNIC | CHAR(1), | /* PATIENT ETHNICITY | 25 - 14 | | 165 */ |
| EMP_INFO(4), | | | | | |
|    EMP_NAME | CHAR(30), | /* EMPLOYER NAME | 21 - 4&11 | | 166 */ |
|    EMP_ADDR | CHAR(25), | /* EMPLOYER ADDRESS | 21 - 5&12 | | 196 */ |
|    EMP_CITY | CHAR(15), | /* EMPLOYER CITY | 21 - 6&13 | | 221 */ |
|    EMP_STATE | CHAR(2), | /* EMPLOYER STATE | 21 - 7&14 | | 236 */ |
|    EMP_ZIP | CHAR(9), | /* EMPLOYER ZIP | 21 - 8&15 | | 238 */ |
|    EMP_STS | CHAR(1), | /* EMPLOYMENT STAT | 21 - 9&16 | | 247 */ |
| MR_NUMBER | CHAR(17), | /* M/R NUMBER | 20 - 25 | | 494 */ |
| STMT_FRM_DT_1D | CHAR(8), | /* STATEMENT FROM DT | 20 - 19 | | 511 */ |
| STMT_TO_DT_1D | CHAR(8), | /* STATEMENT TO DATE | 20 - 20 | | 519 */ |
| ADM_DATE | CHAR(8), | /* ADMIT DATE | 20 - 17 | | 527 */ |
| ADM_HOUR | CHAR(2), | /* ADMIT HOUR | 20 - 18 | | 535 */ |
| ADM_MIN | CHAR(2), | /* ADMIT MIN | | | 537 */ |
| ADM_TYPE | CHAR(1), | /* ADMIT TYPE | 20 - 10 | | 539 */ |
| ADM_SOURCE | CHAR(1), | /* ADMIT SOURCE | 20 - 11 | | 540 */ |
| ADM_SCHED | CHAR(1), | /* SCHED/UNSCHED ADM | 25 - 15 | | 541 */ |
| DSC_DATE | CHAR(8), | /* DISCHARGE DATE | 25 - 4 | | 542 */ |
| DSC_HOUR | CHAR(2), | /* DISCHARGE HOUR | 20 - 22 | | 550 */ |
| DSC_MIN | CHAR(2), | /* DISCHARGE MIN | | | 552 */ |
| STATE_DSC_STS | CHAR(2), | /* STATE DSC STATUS | 25 - 9 | | 554 */ |

FIG. 11

Medical record

```
         MEDICAL_RECORD,
900 ──── PACKET_ID      CHAR(5),    /* claim packet number              0 */
902 ──── SECTION_ID     CHAR(8),    /* section id - "MEDICAL"           5 */
904 ──── SEQ_NUM        PIC'(4)9',  /* record sequence number          13 */
906 ──── ADM_DIAG       CHAR(7),    /* ADMIT DIAGNOSIS CD    70 - 25   17 */
908 ──── PRM_DIAG       CHAR(7),    /* PRIMARY DIAG CD       70 - 4    24 */
910 ──── OTHER_DIAG(14),
         DIAG_CD        CHAR(7),    /* DIAG CODES      70 - 5:12/79 - 4:9   31 */
         DIAG_IND       CHAR(1),    /* OTH DIAG IND          79 - 10:23     38 */
         DIAG_ANES      CHAR(1),    /* OTH DIAG AFTR ANES    79 - 25:38     39 */
         PRN_PROC_CD    CHAR(7),    /* PRIN PROC             70 - 13       157 */
         PRN_PROC_DT    CHAR(8),    /* PRIN DATE             70 - 14       164 */
         OTHER_PROC(14),
         PROC_CODE      CHAR(7),    /* PROC CDS        70 - 15:23/79 - 4:20  172 */
         PROC_DATE      CHAR(8),    /* PROC DTS        70 - 16:24/79 - 5:21  179 */
         CAUSE_OF_INJ   CHAR(7),    /* EXT CAUSE OF INJ      70 - 26       382 */
         PLACE_OF_INJ   CHAR(7),    /* PLACE OF INJURY       79 - 39       389 */
```

FIG. 12

Payor record

| | PAYOR_DATA_AREA, | | | | |
|---|---|---|---|---|---|
| 920 — | PACKET_ID | CHAR(5), | /* claim packet number | | 0 */ |
| 922 — | SECTION_ID | CHAR(8), | /* section id - "PAYOR" | | 5 */ |
| 924 — | SEQ_NUM | PIC'(4)9', | /* record sequence number | | 13 */ |
| 926 — | SRC_OF_PAYMT | CHAR(2), | /* SOURCE OF PAYMENT CD | 30 - 4 | 17 */ |
| 928 — | PAYR_ID | CHAR(5), | /* PAYOR ID (PLN CD) | 30 - 5 | 19 */ |
| 930 — | PAYR_SUB_ID | CHAR(4), | /* PAYOR SUB ID | 30 - 6 | 24 */ |
| | INS_ID | CHAR(20), | /* CERIF/POLICY#/SS# | 30 - 7 | 28 */ |
| | PAYR_NAME | CHAR(30), | /* PAYOR NAME | 30 - 8 | 48 */ |
| | PLN_GRP_ID | CHAR(17), | /* INS/BLC/COM GRP ID | 30 - 10 | 78 */ |
| | PLN_GRP_NAME | CHAR(25), | /* INSURED'S GROUP NM | 30 - 11 | 95 */ |
| | PLN_ADDR_1 | CHAR(25), | /* INS PLAN ADDRESS 1 | 35 - 15 | 120 */ |
| | PLN_ADDR_2 | CHAR(25), | /* INS PLAN ADDRESS 2 | 35 - 16 | 145 */ |
| | PLN_CITY | CHAR(15), | /* INS PLAN CITY | 35 - 17 | 170 */ |
| | PLN_STATE | CHAR(2), | /* INS PLAN STATE | 35 - 18 | 185 */ |
| | PLN_ZIP | CHAR(9), | /* INS PLAN ZIP | 35 - 19 | 187 */ |
| | PLN_PHONE | CHAR(14), | /* phone# aaaxxxxxxx Ext4 | 86 - 11 | 196 */ |
| | PRM_PAYR_CD | CHAR(1), | /* PRIM PAYOR CD | 30 - 9 | 210 */ |
| | INSRD_LNM | CHAR(20), | /* INSURED'S LST NAME | 30 - 12 | 211 */ |
| | INSRD_FNM | CHAR(12), | /* INSURED'S FRST NAM | 30 - 13 | 231 */ |
| | INSRD_MI | CHAR(1), | /* INSURED'S MIDDL I | 30 - 14 | 243 */ |
| | INSRD_SEX | CHAR(1), | /* INSURED'S SEX | 30 - 15 | 244 */ |
| | INSRD_ADDR_1 | CHAR(25), | /* INSURED'S ADDR 1 | 31 - 4 | 245 */ |
| | INSRD_ADDR_2 | CHAR(25), | /* INSURED'S ADDR 2 | 31 - 5 | 270 */ |
| | INSRD_CITY | CHAR(15), | /* INSURED'S CITY | 31 - 6 | 295 */ |
| | INSRD_STATE | CHAR(2), | /* INSURED'S STATE | 31 - 7 | 310 */ |
| | INSRD_ZIP | CHAR(9), | /* INSURED'S ZIP | 31 - 8 | 312 */ |
| | INSRD_DOB | CHAR(8), | /* INSURED'S D-O-B | DGM02 | 321 */ |
| | INSRD_CNTRY | CHAR(2), | /* INSURED'S CNTRY CD | N404 | 329 */ |
| | PAT_RELT_INS | CHAR(2), | /* PAT REL TO INSRD | 30 - 18 | 331 */ |
| | PAT_TO_INS_837 | CHAR(2), | /* REL TO INS 837 TRAN | 30 - 18 | 333 */ |
| | EMPL_NAME | CHAR(30), | /* EMPLOYER NAME | 31 - 9 | 335 */ |
| | EMPL_ADDR | CHAR(25), | /* EMPLOYER ADDRESS | 31 - 10 | 365 */ |
| | EMPL_CITY | CHAR(15), | /* EMPLOYER CITY | 31 - 11 | 400 */ |
| | EMPL_STATE | CHAR(2), | /* EMPLOYER STATE | 31 - 12 | 415 */ |
| | EMPL_ZIP | CHAR(9), | /* EMPLOYER ZIP | 31 - 13 | 417 */ |
| | EMPL_PHONE | CHAR(14), | /* EMPLOYER PHONE | 86 - 10 | 426 */ |
| | EMPL_STS | CHAR(1), | /* EMPLOYMENT STATUS | 30 - 19 | 440 */ |
| | RELS_OF_INFO | CHAR(1), | /* RELEASE OF INFO | 30 - 16 | 441 */ |

FIG. 13

Charge record

```
      CHARGE_RECORD,
940 —— PACKET_ID      CHAR(5),         /* claim packet number                    0 */
942 —— SECTION_ID     CHAR(8),         /* section id - "CHARGES"                 5 */
944 —— SEQ_NUM        PIC'(4)9',       /* record sequence number                13 */
946 —— ACMD_ANC_ID    CHAR(1),         /* "A" - Accomodation Rates              17 */
                                       /* "C" - CPT-4 Codes                        */
                                       /* "I" - ICD9 Codes                         */
948 —— REV_CODE       CHAR(4),         /* ACMD/ANCL REV CD      50 - 4/60/61    18 */
950 —— SERV_DATE      CHAR(8),         /* ANCIL SRVC DATE            61 - 9     22 */
        PROC_OR_ICD9  CHAR(11),        /* HCPCS code                   60/61    30 */
        MOD1          CHAR(2),         /* modifier 1                             41 */
        MOD2          CHAR(2),         /* modifier 2                             43 */
        MOD3          CHAR(2),         /* modifier 3                             45 */
        MOD4          CHAR(2),         /* modifier 4                             47 */
        ACMD_RATE     PIC'(6)z9v.99-', /* ACM RATE                   50 - 5     49 */
        FORM_LOC_49   CHAR(4),         /* FORM LOCATOR 49       50 - 9/60/61    60 */
        UNITS_DAYS    PIC'(3)z9v.99-', /* ACM DYS/ANC UNTS         50/60/61     64 */
        TOT_CHGS      PIC'(7)z9v.99-', /* ACMD TOT CHGS         50 - 7/60/61    72 */
        NON_CVD_CHGS  PIC'(7)z9v.99-', /* ACM NON COVD          50 - 8/60/61    84 */
```

FIG. 14

Occur Code record

```
      OCCUR_CODE_RECORD,
960 —— PACKET_ID      CHAR(5),    /* claim packet number         0 */
962 —— SECTION_ID     CHAR(8),    /* section id - "OCURCODE"     5 */
964 —— SEQ_NUM        PIC'(4)9',  /* record sequence number     13 */
966 —— OCCUR_CODE     CHAR(4),    /* OCCURRENCE CODE            17 */
968 —— DATE           CHAR(8),    /* OCCURRENCE DATE            21 */
```

FIG. 15

Span Code record

```
          SPAN_CODE_RECORD,
980 ——PACKET_ID        CHAR(5),    /* claim packet number        0 */
982 ——SECTION_ID       CHAR(8),    /* section id - "SPANCODE"    5 */
984 ——SEQ_NUM          PIC'(4)9',  /* record sequence number    13 */
986 ——SPAN_CODE        CHAR(4),    /* SPAN CODE                 17 */
988 ——FROM_DATE        CHAR(8),    /* START DATE                21 */
990 ——TO_DATE          CHAR(8),    /* END DATE                  29 */
```

FIG. 16

Cond Code record.txt

```
          COND_CODE_RECORD,
830 ——PACKET_ID        CHAR(5),    /* claim packet number        0 */
832 ——SECTION_ID       CHAR(8),    /* section id - "CONCODE"     5 */
834 ——SEQ_NUM          PIC'(4)9',  /* record sequence number    13 */
836 ——COND_CODE        CHAR(4),    /* CONDITION CODE            17 */
```

FIG. 17

HEALTHCARE FINANCIAL DATA AND CLINICAL INFORMATION PROCESSING SYSTEM

This is a non-provisional application of provisional application Ser. No. 60/373,073 by D. Fitzgerald et al. filed Apr. 16, 2002.

FIELD OF THE INVENTION

This invention concerns a system for interacting with clinical events in acquiring, validating and processing claim data for payment for provision of services to patients by a healthcare provider, for example.

BACKGROUND OF THE INVENTION

An important function performed by healthcare providers (such as hospitals, clinics or physicians) is the sending of claims to healthcare payer institutions to obtain reimbursement for provision of services to a patient. These claims may be in electronic or paper format. Paper claims typically go through a data entry process that converts them to an electronic format. The entered electronic claims are usually sorted, indexed and archived. Each claim is processed in a payer institution adjudication system. The payer adjudication system interprets the claim data and determines whether or not the claim is to be paid in full, partially paid or denied. This adjudication process may be fully automated, partially automated, or manual. The results of claim adjudication may include the issuance of a check and an explanation of benefits (EOB) to the insured and healthcare provider, or a request to send additional information. The process of reviewing claims is labor-intensive and error-prone.

Known adjudication systems help payers and providers streamline their claims payment and medical case management processes. A typical adjudication system employed by a payer institution, may use high speed scanning equipment and optical character recognition software to translate paper claims into electronic data. The electronic claim data is processed by rule based software to interpret the claim data for any conflicts. Healthcare providers do their best to ensure claims are accurate before they send them to the payer by embedding payer rules into their software applications or by utilizing "claim scrubbing" applications to evaluate claim data prior to submission to the payer. Known systems also approach claim data processing from a piecemeal perspective whereby, for example, one software vendor system addresses online eligibility and electronic remittance and a different vendor system addresses revenue management from a physician perspective. Another vendor system supports claim editing, but only after the claim is generated. Further known systems require significant user intervention once a claim is produced.

Known systems fail to approach claims processing and management from a combined payer, provider and patient perspective. Prior solutions approached the problem from a piecemeal perspective and failed to interact dynamically with clinical events and clinical information systems in the healthcare provider environment. Typically one vendor system addresses automated eligibility and a separate vendor system supports electronic payment, for example and an overall result is that there is inefficiency and error introduced through the lack of financial system and clinical system interaction. This results in claims that fail the edit process upon receipt by the payer and consequent disallowance by the payer. Disallowed claims cause delayed payment and negatively impact healthcare provider cash flow and patient satisfaction with the process. A system according to invention principles improves clinical and financial data processing operation interaction and thereby claim accuracy prior to claim submission to a healthcare payer institution.

SUMMARY OF INVENTION

A patient claim data processing system employed by a healthcare provider responds to and initiates clinical events and attains early accurate claim data during a patient healthcare encounter cycle to support prompt claim data validation and editing both for individual claim elements and for a completed claim to improve claim accuracy prior to claim submission to a payer. A system processes financial data related to provision of healthcare to a patient in response to clinical events and services. The system includes an interface processor for receiving a message identifying an event and a related change in healthcare data concerning a patient and also includes a source of rules for determining characteristics associated with reimbursement for provision of an individual service to a patient. A rules processor initiates application of a rule derived from the rules source to process financial data concerning provision of the individual service to the patient in response to receiving the message identifying the event. A result processor initiates an action in response to a result derived by the application of the rule to process the financial data.

In a feature of the invention the rules processor also validates the financial data complies with the rule.

BRIEF DESCRIPTION OF THE DRAWING

FIG. 4 shows a user interface display image illustrating a patient claim billing record for multiple patient encounters with a healthcare provider concerning treatment of an injury, according to invention principles.

FIG. 5 shows exemplary claim data processing rules associated with clinical events occurring to a patient, according to invention principles.

FIG. 6 shows exemplary claim data processing rules interacting with payer actions and used to initiate automated payment collection, according to invention principles.

FIGS. 11-17 show data records including data elements incorporated in a central data repository used in claim processing, according to invention principles.

DETAILED DESCRIPTION OF INVENTION

Figure 1:
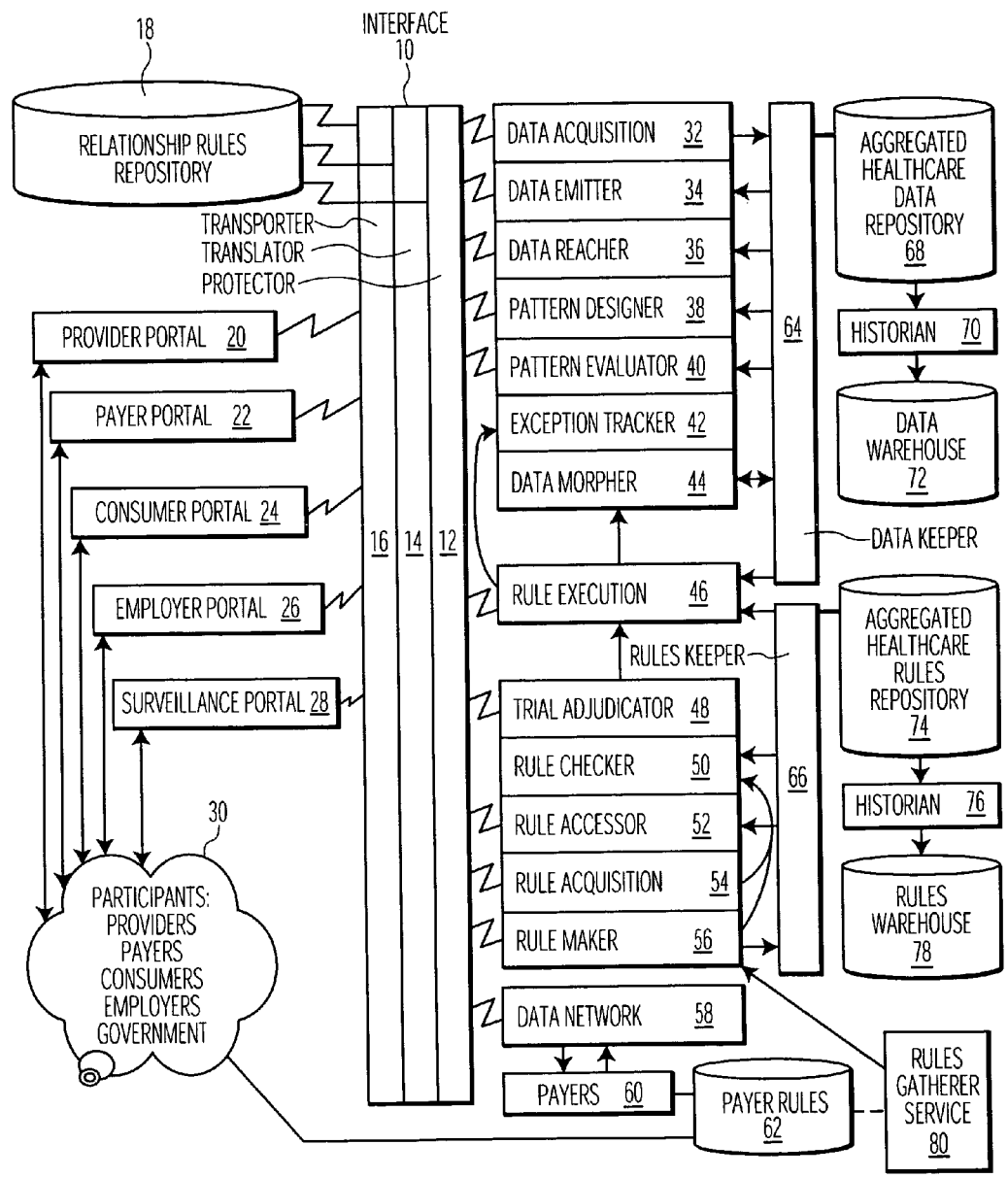
FIG. 1 shows a claim processing system that responds to and initiates clinical events during a patient healthcare encounter cycle to improve claim accuracy prior to claim submission to a healthcare payer institution or other entity, according to invention principles.

FIG. 1 shows an overall claim processing system that responds to and initiates clinical events during a patient healthcare encounter cycle to improve claim accuracy prior to claim submission to a healthcare payer institution or other entity. The system performs trial adjudication on a claim to improve claim accuracy prior to claim submission to a healthcare payer institution or other entity. In the FIG. 1 system, continuously updated centralized common rules in repository 74 are employed to ensure that individual healthcare providers, as well as individual healthcare payer institutions are working with the most up-to-date version of the rules. Use of centralized rules ensures that a healthcare provider is able to comply with the latest provisions of the rules. A rule as used herein includes a procedure for determining that healthcare claim elements comply with predetermined requirements including, health plan reimbursement conditions, health plan format requirements, a reimbursement formula, reimbursement constraints and a reimbursement computation procedure. A rule also may include a prescribed guide, a precept, or a model for how to present, conduct or regulate an action by using a form and data or the relations between form and data. Further, an exception as used herein encompasses the identification of an issue and mechanism to process that issue.

The system of FIG. 1 responds to, and initiates, clinical events during a patient healthcare encounter cycle to attain accurate claim data at an early and appropriate time. A rule execution unit responds to clinical and other events, to perform multiple functions. The rules determine, affect or govern processing of authorization, data content, contract terms, compliance with information sufficiency requirements, compliance with format requirements and communication connectivity. The system advantageously eliminates or reduces manual involvement in reviewing eligibility denials, researching payment denials, checking of error reports, claim mailing, and manual payment posting and expedites accurate claim generation, submission and reimbursement.

The FIG. 1 system automates the pre-registration, eligibility, registration authorization, claim generation, trial adjudication, claim submission, payment remittance, and post-remittance processes of a health care claim data processing cycle to provide seamless, accurate and prompt processing. The system automates coordination of employer and payer activities and ensures that pre-visit enrollee data is accurate. Thereby, if a patient uses a consumer portal (24) to schedule a visit or if a healthcare facility collects insurance information from a patient, medical necessity, referral and eligibility verification processing is automatically initiated. A claim is evaluated for accuracy and edited by a rule execution function 46 and adjudication unit 48, using the applicable rules in rules repository 74, both before the claim is completed (i.e. as individual claim elements for individual healthcare encounters post to the claim, for example) and again before the completed claim is submitted for payment. A variety of portals 20-28 in the FIG. 1 system are controlled and administered by interface 10 to provide claim data access to patients, payers, providers, employers and government agencies. The system facilitates healthcare provider compliance with governmental and payer rules through use of automated, rules-based editing and review systems.

The FIG. 1 system comprises functions implemented in software applications and executable procedures for processing claim data. These functions may also be implemented in hardware or a combination of both hardware and software resident in one or more computer systems and servers and involving one or more communication networks for internal and external communication. The system processes claim data related to provision of healthcare to a patient by collating data related to a claim for a particular patient for submission to a payer. The collated claim data is submitted for pre-processing using rules to validate the collated claim data is in condition for processing to initiate generation of payment. Upon successful validation the validated claim data is submitted to a payer. The claim data is collated by data acquisition unit 32 via interface 10 for storage in data repository 68. Repository 68 contains financial and clinical data related to healthcare encounters that are currently ongoing. Data acquisition unit 32 is able to receive both solicited and unsolicited data from multiple different sources and to request data from these sources via interface 10. The different sources include external users (participants) subscribing to and using the FIG. 1 system and may include for example, healthcare providers, healthcare payer institutions (e.g. insurance companies, Health Maintenance Organizations—HMOs etc.), consumers, employers, and government agencies.

Data keeper unit 64 acts as a gateway and data management system governing data storage and retrieval for healthcare data repository 68 and processing requests to use repository 68 to store, modify, and retrieve data. Placement of Data Keeper (64) between the Data Repository (68) and the other system components, allows the design of the data repository (68) to change with zero impact on the rest of the system, except for the Data Keeper (64) alone. Data keeper unit 64 also tracks data changes in repository 68 by recording time, date and nature of changes made as well as the source and identity of the author of the changes to maintain a data update audit trial. Historian unit 70 is used in archiving and maintaining older data value versions and is specifically used in archiving data records associated with patient encounters following completion of financial transactions (i.e. encounters for which no related financial transactions are outstanding) and processing for these encounters. An encounter as used herein comprises a patient encounter with a healthcare enterprise involving patient and healthcare enterprise interaction that has a financial or transaction consequence and may include for example a patient visit, phone call, inpatient stay or outpatient treatment etc. Records of such encounters are maintained by data keeper unit 64 in repository 68. Historian unit 70 stores archived data in archive (data warehouse) database 72.

Rule execution unit 46 executes rules derived from rules repository 74 via interface 66 to automatically perform multiple functions in response to clinical and other events. These functions include, for example, initiation of, patient eligibility verification (for insured coverage of a particular procedure), proposed procedure medical necessity verification as well as referral processing. Also, in response to clinical and other events, unit 46 validates individual claim elements as they are incorporated into a claim and performs other actions. Unit 46, in conjunction with trial adjudication unit 48, also validates a completed claim as a whole.

Figure 2:
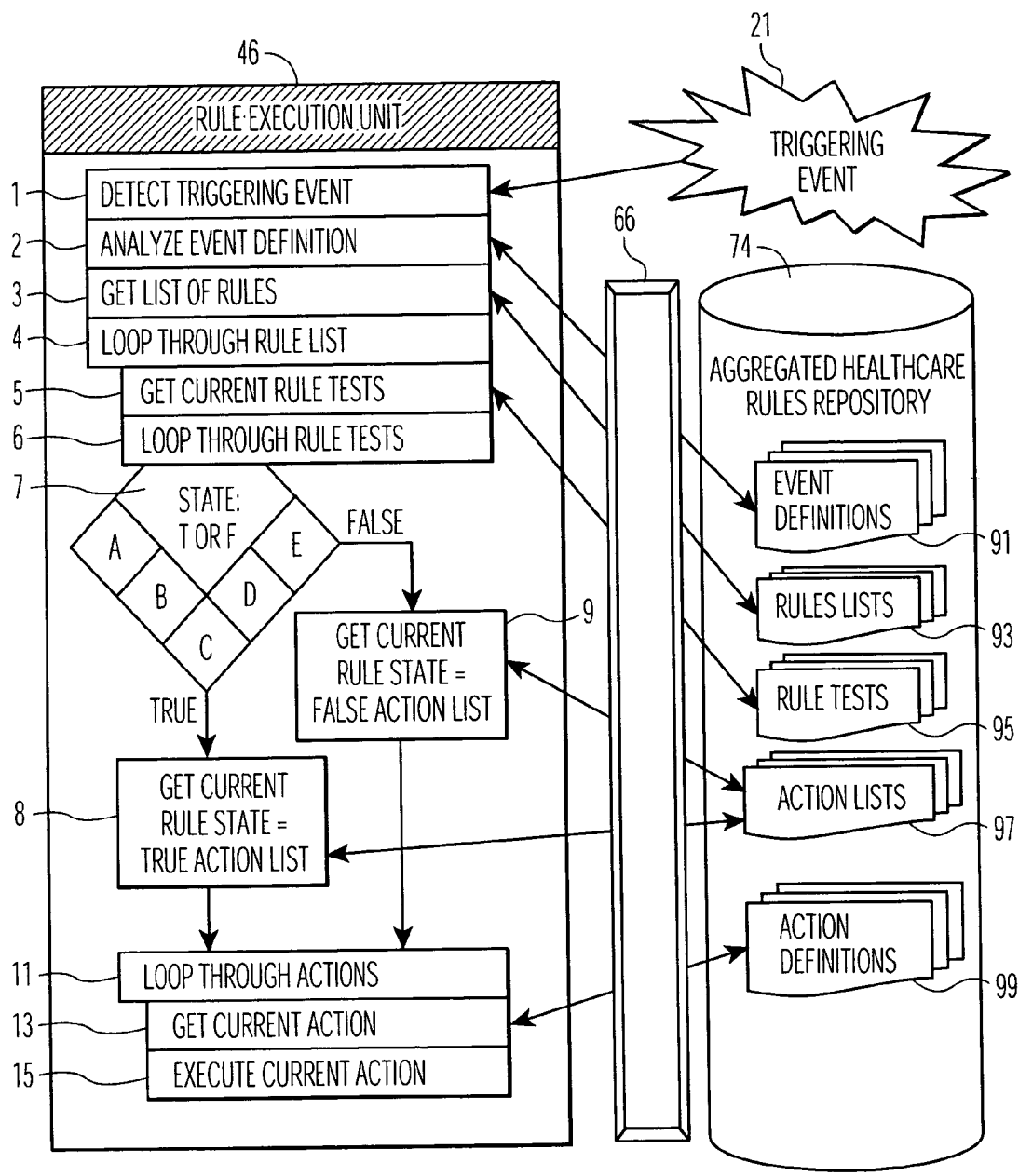
FIG. 2 shows a rule execution system that responds to and initiates clinical events during a patient healthcare encounter cycle, according to invention principles.
Figure 3:
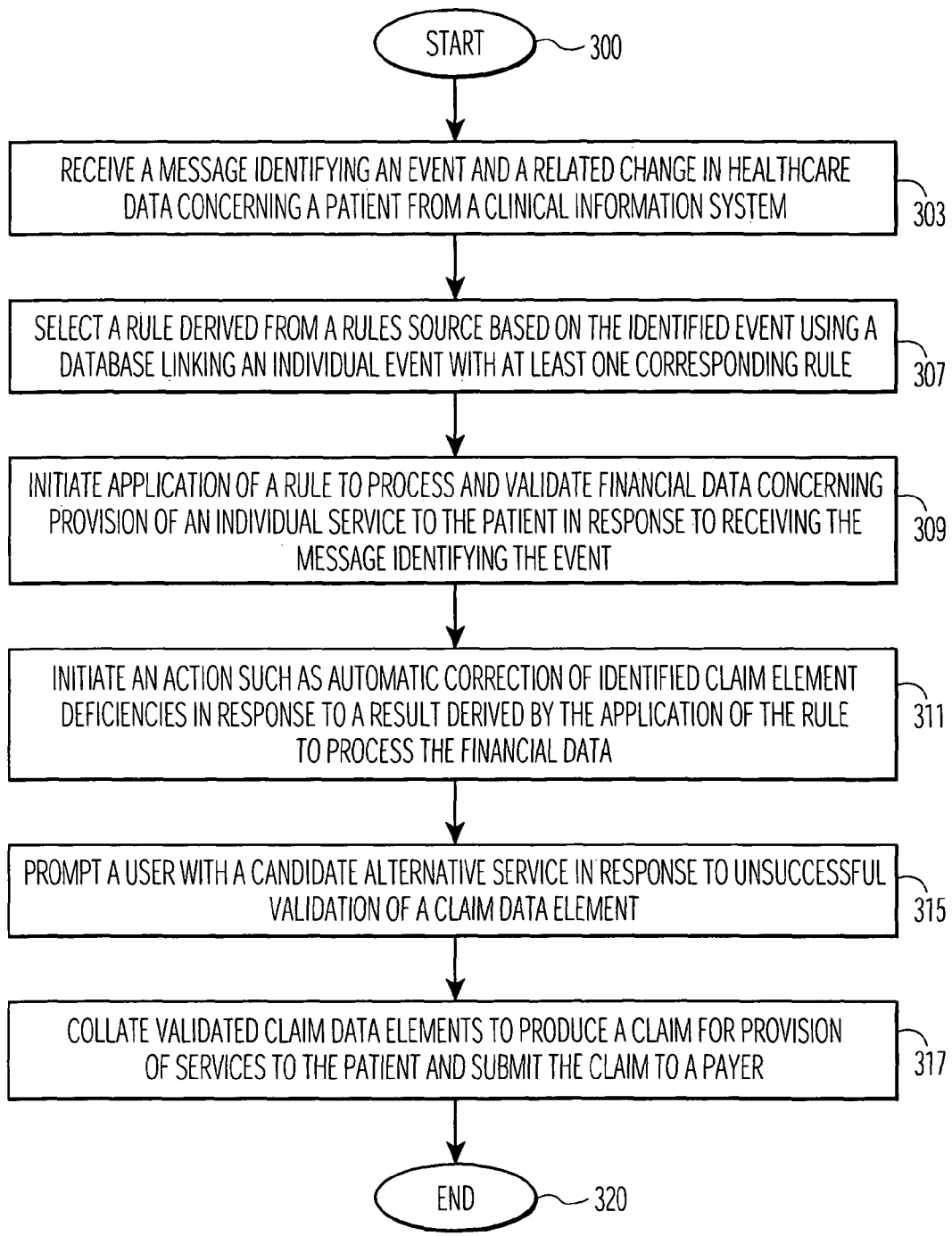
FIG. 3 shows a flowchart of a process employed in claim processing by the systems of FIGS. 1 and 2, according to invention principles.

FIGS. 2 and 3 illustrate the operation of unit 46 and its interaction (FIG. 1) with clinical events occurring during a patient healthcare encounter cycle as recorded in a clinical information system (not shown to preserve drawing clarity).

Specifically, FIG. 3 shows a flowchart of a process executed by unit 46 as detailed in FIG. 2. Considering FIGS. 2 and 3 together, in step 303, following the start at step 300, unit 46 receives a message identifying an event (item 21 of FIG. 2) and a related change in healthcare data concerning a patient. Unit 46 detects the triggering event message (item 1 FIG. 2) and analyzes (2) the event identifier to select (3) one or more rules in step 307 from rule lists (93 FIG. 2) in rule repository 74 using a database 91 linking an individual event with at least one corresponding rule. An event comprises performance of data entry or update, transmission of a file, automatic performance of a rule directed action, the expiration of a specified time interval or scheduling of an action. Specifically, an event may include (a) generation of a record associated with provision of a service to patient, (b) generation of a billing related record for provision of a service to patient, (c) generation of an indication of occurrence of provision of healthcare to a patient by an operating process, (d) generation of an indication of occurrence of provision of healthcare to a patient by patient monitoring equipment and (e) generation of an indication of occurrence of provision of healthcare to a patient by a medical device. A rule executed by unit 46 may itself generate a triggering event and initiate execution of other rules. The rules are used to determine characteristics associated with reimbursement for provision of an individual service to a patient. Such characteristics include, for example, (i) an expected reimbursement amount for provision of an individual service to a patient, (ii) an effective benefit period for the reimbursement, (iii) contract constraints for the reimbursement, (iv) an indication that the provision of the individual service to the patient qualifies for reimbursement under a particular insurance plan and (v) an indication the provision of the individual service to the patient is linked to provision of other services to the patient.

FIGS. 5 and 6 show exemplary claim data processing rules associated with clinical events occurring to a patient and used to initiate automated payment collection respectively. Specifically, rules 501-513 in FIG. 5 are employed by unit 46 to automatically validate and correct claim data for provision of services to a patient in response to triggering events. Claim data is processed by calculating expected reimbursement for services rendered to a patient one service at a time. In response to a record of a charge for a service being incorporated in a patient billing record, an expected reimbursement is computed for those active healthcare insurance policies that are applicable in order of their priority. Unit 46 executes rules 501-513 and other rules to validate compliance of claim data with payer requirements. Unit 46 does this for both individual service charges as they accumulate in a patient billing record and for an overall claim covering multiple services and associated charges.

Rules 521-530 in FIG. 6 are employed by unit 46 to automatically initiate payment collection to pursue monies owed by insurance payers or other responsible parties. Other rules that may be initiated by unit 46 address, formatting and transmission of insurance claims, transaction recording, payment variance processing and remittance processing. The system of FIG. 1 automatically processes electronic remittance data including insurance payer remittance explanation codes that are used by unit 46 for rule selection and initiation to process payments, adjustments, comments, and other items received from a healthcare payer organization, for example. Unit 46 also executes rules targeted to discover and recover charges that were not made or were otherwise not successfully conveyed to a responsible payer. Specifically, unit 46 executes rules to identify, (a) records of patient encounters with no corresponding record of a charge being made, (b) a surgery charge without an anesthesia charge and (c) an ICD9-CM procedure code indicating a surgical procedure but no surgery and/or anesthesia charge being made, for example.

In step 309 (FIG. 3) unit 46 initiates application of rules selected in step 307 to process financial data concerning provision of an individual service to a patient in response to the received event identification message. The financial data is claim data together with patient and clinical service identification data for provision of a specific service to a particular patient. The financial data as used herein comprises, a portion of a claim, a complete claim, individual records of a claim or record data associated with an individual patient encounter with a healthcare service provider. FIG. 4 shows a user interface display image illustrating financial data for a particular patient (the patient is identified by item 420). The billing record includes collated claim data elements for multiple patient encounters 402, 404 and 406 with a healthcare provider concerning treatment of an injury. FIG. 4 also displays messages generated as a result of the application of editing rules (executed by unit 46) applied to this set of claim data. The rules have established two levels of severity in these messages: errors, that are to be corrected, and warnings, that need to be reviewed.

Unit 46 in step 309 (FIG. 3) initiates successive sequential execution of rules selected in step 309 (item 4 FIG. 2). However, a rule may itself alter a sequence of rule execution, such as by directing that processing continue from an identified rule other than a subsequent rule in a rule list or a rule may result in insertion one or more additional rules into a sequence. Alternatively, a rule may direct termination of execution of a rule sequence, for example. The execution of a rule involves deriving the tests that comprise an individual rule (item 5 FIG. 2) from test repository 95 and successively executing (item 6 FIG. 2) the individual tests that comprise an individual rule. An individual validation rule may contain one or more tests to identify a true condition and initiate an associated first set of actions or a false condition and initiate an associated second set of actions. A rule test condition may be simple or complex involving a combination of tests linked with logical operators (e.g., "and," "or," "not"). Individual linked tests results are logically combined to provide an overall test result (of true or false). Further, a set of actions may be an empty set triggering no actions. If a trigger condition is not detected a rule default true condition is declared. Rules repository 74 includes executable rules and the test components incorporated within the individual rules together with an English language description documenting individual rule function for use in help prompts and explanation to non-technical users and other users. A start and end date and time indicating a period of validity is also maintained by repository 74 for both a rule and individual test components incorporated by the individual rule. Unit 46 examines rule validity periods and does not execute a rule or test component at a time and date falling outside of a period of validity.

Unit 46 successively executes tests (item 6 in FIG. 2) derived from test repository 95 that comprise an individual rule and logically combines the test results to provide an overall test result (of true or false) as shown in item 7 of FIG. 2. Specifically, unit 46 evaluates an individual test component (shown in the diagram as A, B, C, D, E within a decision structure) and applies stored logical relationships (stored with the tests in test repository 95) to determine an overall result state for an individual rule. Upon determination of a rule true state, unit 46 executes a first set of actions (step 8 of FIG. 2) and in response to determination of a rule false state unit 46 executes a second set of actions (step 9 of FIG. 2).

In step 311 (FIG. 3) unit 46 successively initiates actions in steps 11-15 of FIG. 2 that are determined based on a rule result using action identification repository 97. For this purpose, unit 46 initiates actions in step 15 that are specified in data derived from action definition repository 99 in step 13 using identification data derived from repository 97 via rule interface 66. One such action is the automatic correction of identified claim element deficiencies determined in response to applying the rules. The rules automatically make corrections to claim data that are compatible with the Correct Coding Initiative (CCI) Edits Version 8.1 of Apr. 1, 2002 of the Centers for Medicare & Medicaid Services (CMS) involving identifying and eliminating incorrect coding of medical services. The CMS requires compliance with the CCI edits to receive payment from Medicare and Medicaid. Unit 46 executes rules incorporating the CCI edits and applies them to the clinical codes submitted on claims. Additional claim editing rules employed by unit 46 are derived from CMS Comprehensive/Component Edits (CCE) that are compatible with the Correct Coding Initiative (CCI) Edits Version 8.1. These additional claim editing rules examine codes identifying a bundle of services or the codes that identify the individual components of the bundle. In this scheme either the individual components or the bundle may be coded, but not both. Additional claim editing rules employed by unit 46 comprise CMS Mutually Exclusive Code (MEC) Edits (compatible with the Correct Coding Initiative (CCI) Edits Version 8.1) that identify pairs of procedures that are not both reimbursed when rendered by the same provider on the same date of service.

Other actions initiated by unit 46 comprise addition of a task to a healthcare worker worklist or removing a task from the worklist. An exemplary message adding a worklist item may comprise, for example, "Prepare bed A in room 421 for arrival of patient John Doe. ETA 8:00 PM on Apr. 16, 2002." Another task may involve review of data derived as a result of application of a rule to process patient financial data, for example. The data for review may comprise, a notification of denial of a particular treatment for a patient, a notification of a requirement for a waiver to be provided for qualification of a treatment for reimbursement, or a result of processing a trial claim for reimbursement for a particular treatment for a patient. Alternatively, a task (such as initiation of an infusion drip feed, for example) may be scheduled for performance by medical apparatus or removed from scheduled performance by medical apparatus. Other actions that are initiated by unit 46 include, linking a record of a pre-admission test to a record of a surgical procedure, linking a record of a same day surgery procedure to a record of an inpatient encounter, linking a record identifying a mother to a record associated with a newborn baby or linking a record of an outpatient procedure to an inpatient encounter occurring on the same day. Additional actions that may be initiated by unit 46 include, creation of worklists of tasks for automatic performance, creation of logs and audit reports and accounting reports, creation of error reports, generation of claims, posting of remittances, modification of data, and other actions.

In step 315 (FIG. 3) unit 46 prompts a user with a candidate alternative service in response to an unsuccessful validation (in step 309) of a claim data element for provision of a particular service. Unit 46 in step 317 initiates collation of validated claim data elements to produce a claim for provision of services to a patient for submission to a payer. The process of FIG. 3 ends at step 320.

Figure 7:
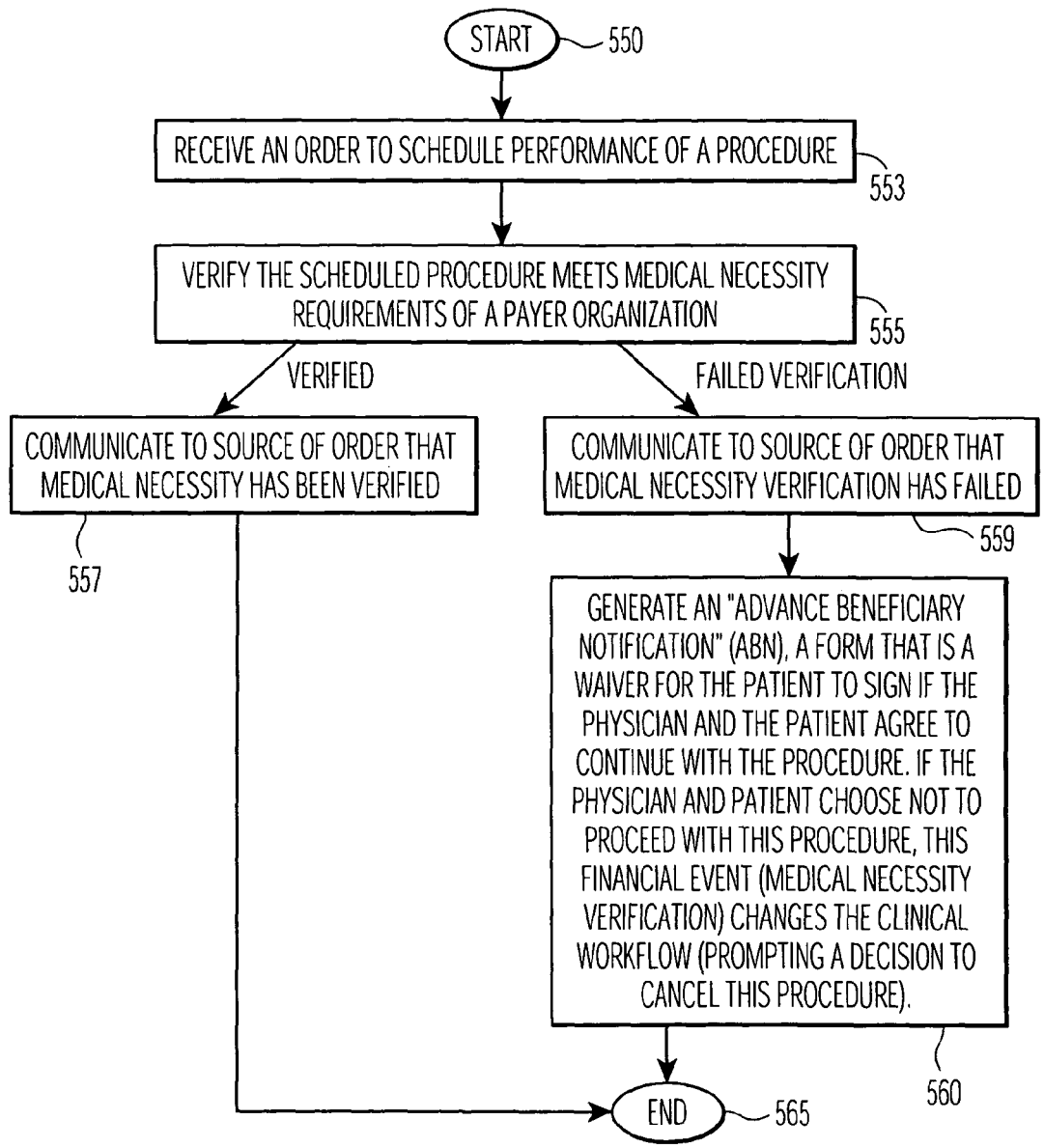
FIG. 7 shows a flowchart of a process, having clinical and financial consequences, employed in checking whether a proposed procedure meets medical necessity requirements of a payer, according to invention principles.

FIGS. 7-10 show rule directed processes involving clinical system and financial system interaction initiated by unit 46 through execution of rules in the manner described in connection with FIGS. 2 and 3. FIG. 7 shows a flowchart of a process, having clinical and financial consequences, employed in checking whether a proposed procedure to be performed for a patient meets medical necessity requirements of a payer. A receipt of an order to perform a process entered into a hospital information system advantageously automatically triggers medical necessity determination by unit 46. For this purpose, data associated with the order is examined and a source of the order is notified if the examination identifies a problem with the order format or content. The receipt of the order may also advantageously automatically trigger a trial adjudication of claim data for the procedure. In FIG. 7, after the start at step 550 and receipt of an order in step 553, unit 46 executes rules in step 555 in response to the order receipt event to verify the scheduled procedure meets medical necessity requirements of a particular payer organization. Unit 46 initiates communicating to the source of the order that either, medical necessity for the associated procedure has been verified in step 557 or that medical necessity verification failed in step 559. Upon a failure in step 559, unit 46 in step 560 initiates generation of an "Advance Beneficiary Notification" (ABN), a form that is a waiver for the patient to sign if the physician and the patient agree to continue with the procedure. If the physician and patient choose not to proceed with this procedure, this financial event (medical necessity verification) changes the clinical workflow (prompting a decision to cancel this procedure). The process of FIG. 7 ends at step 565.

Figure 8:
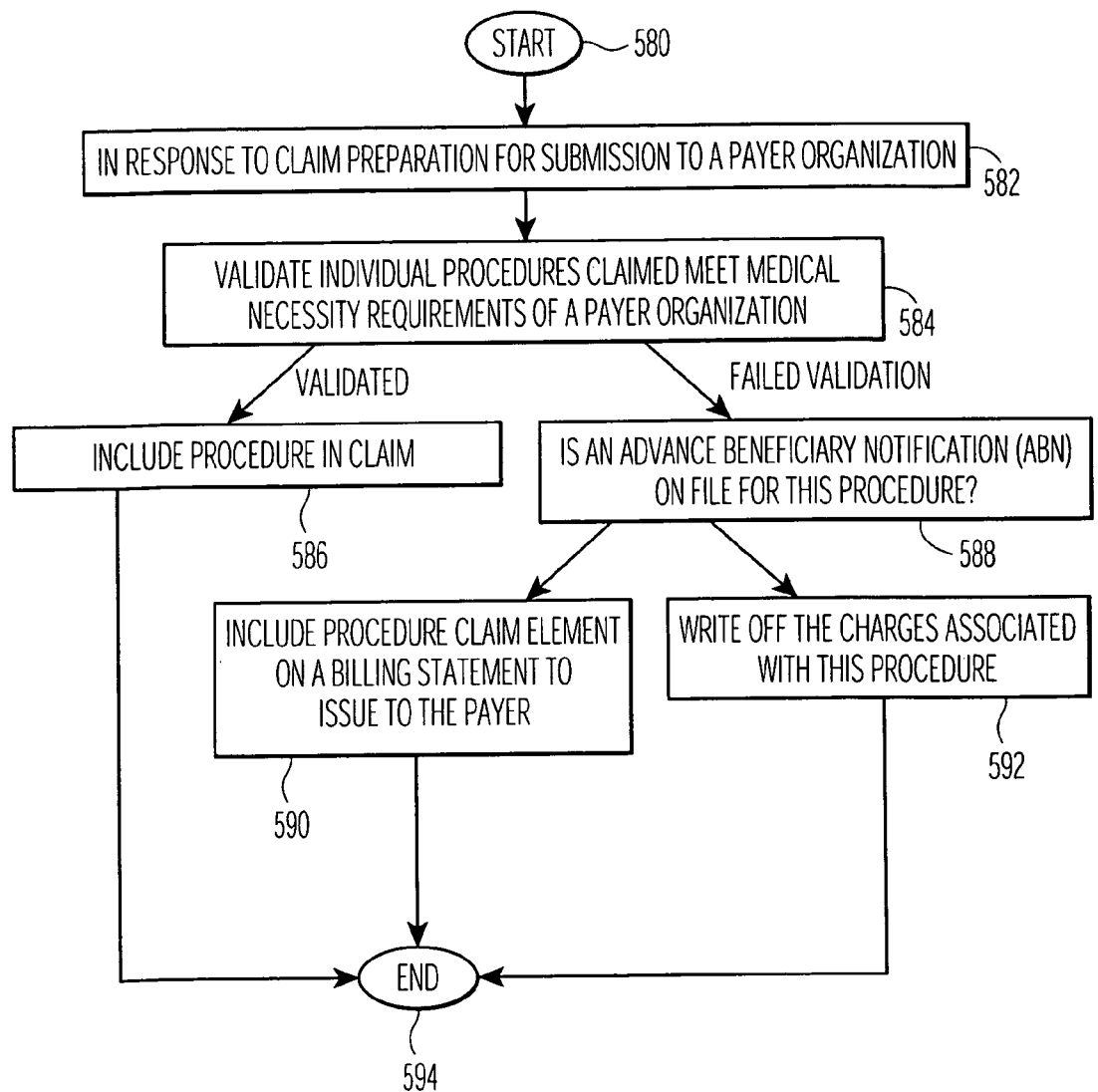
FIG. 8 shows a flowchart of a process, having clinical and financial consequences, employed in validating a claim data element for a performed procedure, according to invention principles.

FIG. 8 shows a flowchart of a process, having clinical and financial consequences, employed in validating a claim data element for a performed procedure. In FIG. 8, after the start at step 580 and in response to preparation of a claim for submission to a payer in step 582, unit 46 executes rules in step 584 to validate that individual procedures that are claimed meet medical necessity requirements of a payer organization. The claim elements for procedures that have been verified for medical necessity in step 584 are directed by unit 46 to be included in the claim for submission to a payer in step 586. Unit 46 in step 588 determines whether a record exists of an Advance Beneficiary Notification for those procedures that have failed medical necessity verification in step 584. If such a notification is determined to exist for these particular procedures, unit 46 in step 590 directs that the claim elements associated with these particular procedures are included in a claim for submission to a payer. Unit 46 in step 592 directs that no billing is to be made for those procedures for which such a notification does not exist. The process of FIG. 8 ends at step 594.

Figure 9:
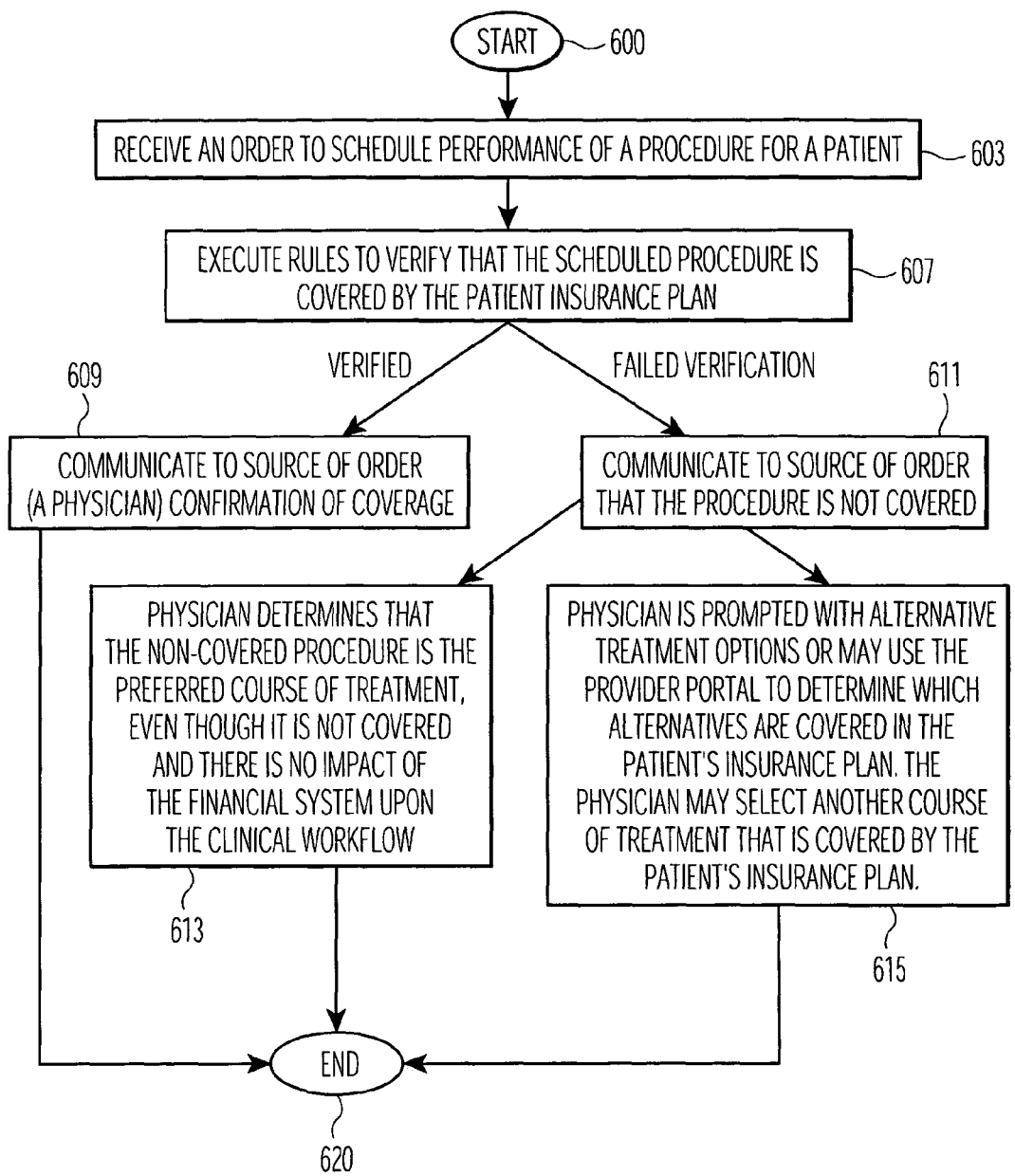
FIG. 9 shows a flowchart of a process, having clinical and financial consequences, employed in determining whether a proposed procedure is covered by a patient healthcare plan, according to invention principles.

FIG. 9 shows a flowchart of a process, having clinical and financial consequences, employed in determining whether a proposed procedure is covered by a patient healthcare plan. Unit 46 executes rules to advantageously automatically verify that a patient is eligible for reimbursement for a visit or procedure under a patient medical insurance plan. This is done in response to receipt of a message indicating a patient visit or procedure is scheduled and insurance information is collected. In FIG. 9, after the start at step 600 and receipt of an order scheduling a patient visit or procedure and collection of insurance information in step 603, unit 46 executes rules in step 607 to verify that the scheduled visit or procedure is reimbursable under the patient medical insurance plan. Unit 46 initiates communicating to the source of the order (e.g., a physician) that either, insurance coverage of the visit or procedure has been verified in step 609, or that the visit or procedure is not covered in step 611. If the patient is ineligible for the service based on contract terms, a worklist entry may also be created for review by expert personnel at a later time. Unit 46 uses, previously collected patient insurance information identifying a payer together with stored payer address information, to send eligibility requests to the identified payer. Individual healthcare providers determine rules concerning how long to wait for an eligibility response before initiating further actions (such as making a worklist entry, sending an e-mail, etc.) to expedite a response. Upon a non-coverage determination in step 611, a physician in step 613 may determine that the non-covered procedure is the preferred course of treatment, even though it is not covered. In this case, there is no impact of the financial system upon clinical workflow. Alternatively, upon a non-coverage determination in step 611, a physician is prompted with alternative treatment options in step 615. The physician may use the provider portal 20 (FIG. 1) to determine and select an alternative treatment which is covered by the patient insurance plan. Thereby the financial system alters the clinical workflow. The process of FIG. 9 ends at step 620.

Figure 10:
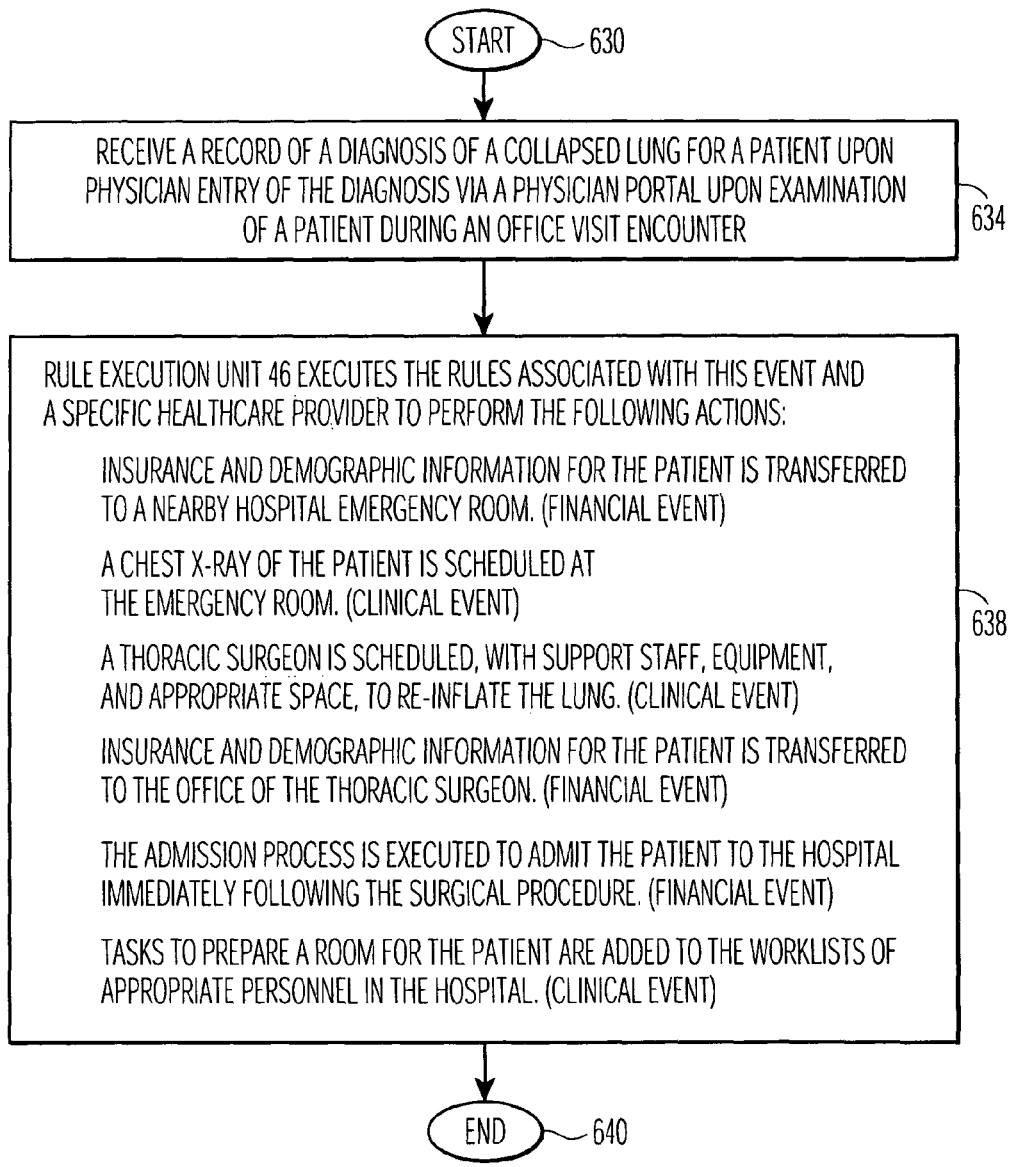
FIG. 10 shows a flowchart of an action execution process resulting from generation of a medical diagnosis record, according to invention principles.

FIG. 10 shows a flowchart of an action execution process resulting from generation of a medical diagnosis record for a particular patient. In FIG. 10, after the start at step 630 and receipt of a record of a diagnosis (indicating a collapsed lung, for example) in step 634, unit 46 executes rules in step 638 to initiate actions in response to the diagnosis event. The actions initiated involve, for example, transferring patient information, scheduling an X-ray, scheduling surgeon availability, executing patient admission, and scheduling personnel to prepare a room by incorporating tasks on worklists. The process of FIG. 10 ends at step 640. Other actions which may be initiated by unit 46 in response to diagnosis entry, for example, include generation of real time notifications to a specified recipient, via e-mail, pager, or PDA device. An exemplary notification might be, for example, "Dr. Smith, your patient John Doe arrived at Hospital xyz Emergency Room at 7:05 PM on Apr. 16, 2002. He was diagnosed with a fractured left tibia. The bone was set and a cast applied. The Emergency Room physician who performed these procedures was Dr. Jones." In addition unit 46 may initiate, setting off of an alarm, preparation of periodic reports, alteration of patient census records, triggering of another event such as a patient admission event and execution of associated rules to transfer the patient from the emergency room to the assigned bed, etc.

Continuing with FIG. 1, collated claim data is submitted for pre-processing by trial adjudicator 48 using unit 46 to execute rules in the manner previously described in connection with FIGS. 2 and 3. The pre-processing validates the collated claim data is in condition for processing to initiate generation of payment. Data Morpher unit 44 comprises a sub-category of actions that rules invoke to modify data in repository 68 in response to command. Unit 46 also processes and executes rules stored in the Relationship Rules Repository 18 that contains rules required and used by the Protector 12, Translator 14, and Transporter 16 during communication involving interface 10.

Rules including regulatory guidelines and directives are continuously acquired for storage in repository 74 and are continuously updated and maintained in this repository via rules keeper unit 66. Rules archiving unit 76 in conjunction with unit 66, dates and time stamps rules to be archived and stores obsolete, expired or older version rules in archive (rules warehouse) database 78. Repository 74 also contains adjudication rules acquired from payer institution participants and rules that are established from previous transactions with payers. Repository 74 further contains rules developed by the system and by authorized participants that add automated processes to the system. Pattern Designer unit 38 creates specialized rules that define surveillance research processes and rule maker unit 56 is used to create general purpose rules.

Unit 48 uses rules in repository 74 derived from external rule sources (such as rules 62 owned by a payer institution 60) by rule accessor 52 via interface 10 and data network 58. Network 58 may comprise a conventional network such as LAN (local area network), WAN (wide area network) or the Internet or alternatively may comprise a network service such as a clearinghouse or other service used by a healthcare payer or a healthcare provider to facilitate data and rule (e.g., payer rules 62) acquisition for claim adjudication. Payer rules 62 are rules promulgated by a payer 60 that are not accessible through the automated process managed by Rule acquisition unit 54. Rather rules 62 are manually determined through manual acquisition processes and are parsed and analyzed by Rule acquisition unit 54 by using a user interface provided by rule maker unit 56. The Rule Maker 56 user interface supports manual creation, review and update of rules including those acquired via unit 54. Unit 56 also prompts a user with lists of available tests and actions and guides the user through the process of constructing and editing rules prior to storing the edited rules in Rules Repository 74.

Rule acquisition unit 54 accumulates rule data (remember unit 54 is also an automated unit that can poll payers systems for rules) through documentation and other information provided by payers that do provide access to their proprietary programmed rule sets. Unit 54 retrieves payer generated information bulletins from payer websites and other sources and analyzes this material to identify information representing new or changed rules for incorporation in repository 74 and to identify rules that have expired. Further, individual payer institutions may use Payer Portal 22 to communicate rule information via interface 10 to acquisition unit 54 which incorporates them using rule keeper unit 66 in repository 74. Unit 54 also receives new rules following user manual data entry and processing via a user interface provided by rule maker 56 based on information acquired from payers by rules gatherer service 80. Payers forward updated rule information to service 80 in advance of implementing a new rule or rule version, for example. Rule Checker unit 50 monitors rules in repository 74 and identifies and indicates to a user those rules that are incomplete or contain incorrect syntax. Unit 50 also reports combinations of rules that are mutually inconsistent. Further, in response to identification of a predetermined exception condition during claim data processing by rule execution unit 46 and trial adjudication unit 48, exception tracker function 42 employs a sub-set of rules managing the processing and reporting of an identified exception condition. Exception tracker function 42 may be invoked by rule execution unit 46 in response to execution of a particular rule or upon a particular result of executing a rule. Upon determination of an exception condition, function 42 may schedule manual intervention, via a user interface or a worklist or by communicating a report or message to a recipient, for example. Function 42 also tracks when exception conditions are removed based on received messages identifying claim data correction updates to patient records, in response to user action, for example.

Claim data processed by unit 46 and ultimately submitted to a payer upon amendment (if required) and validation is derived from data repository 68. FIGS. 11-17 show an exemplary data record structure for data elements incorporated in central data repository 68 and used in claim processing. Specifically, FIG. 11 shows a partial patient record data structure, FIG. 12 shows a medical record data structure and FIG. 13 shows a partial payer record data structure. A charge record data structure and occurrence code data structure are presented in FIGS. 14 and 15 respectively and FIGS. 16 and 17 indicate a span code (for use in identifying service charges that are to be grouped on a single claim) and a medical condition code data structure respectively. These record structures are exemplary only and repository 68 typically contains other types of records associated with claim data such as, for example, records concerning ambulance services, rehabilitation services, treatments and other services and activities. The record structures of FIGS. 11-17 are individually accessible in repository 68 using a claim packet identifier (800, 900, 920, 940, 960, 980, 830), section identifier (802, 902, 922, 942, 962, 982, 832) and sequence number (804, 904, 924, 944, 964, 984, 834).

Data in an individual record data structure, in this example, is field length delimited. In the patient record structure of FIG. 11, for example, a patient last name (806) occupies a fixed length of 20 characters, followed by a patient first name (808) occupying twelve characters and middle initial (810) occupying one character. The record structures of FIG. 12-17 contain data related to other particular claim data aspects in similar predetermined fixed length fields. The medical record of FIG. 12, for example, contains an admission diagnosis code (906), as well as a primary diagnosis code (908) and other diagnosis codes (910). The payer record of FIG. 13 contains a source of payment code (926), as well as payer identifier (928) and payer sub-identifier (930). The charge record of FIG. 14 contains a service charge code (946), as well as a service charge revision code (948) and service date (950). The occurrence code record of FIG. 15 contains an occurrence identification code (966) and occurrence date (968). The span code record of FIG. 16 contains a span identification code (986), as well as a span determination start date (988) and end date (990) for use in identifying code and the related dates that identify an event that relates to the payment of this claim. The condition code record of FIG. 17 contains a medical condition identification code (836). The items referred to in connection with FIGS. 11-17 are described for exemplary purposes. However, other record items are shown in the record structures of FIGS. 11-17. These other items are representative of the breadth of data that may be included in the various records in the repository 68 structure, for example. In an alternative embodiment, other non-fixed length data record structure or another data record structure may be employed for repository 68.

The claim data in repository 68 is collated by data acquisition unit 32 via interface 10 from multiple different sources as previously described and stored in repository 68 via data management system 64. A data emitter unit 34 provides claim data to an external entity (e.g., portals and participants 20-30) by extracting required claim data from repository 68 and communicating it via interface 10. Data reacher unit 36 is used by functions of the FIG. 1 system to provide read-only access to claim data stored by a remote entity and to make decisions based on this data. Further, claim data repository 68 is searchable by participants 30 via external portals 20-28 using data search criteria created using search pattern design function 38. Thereby a user may search for statistically significant data patterns and other data patterns in analyzing the claim data in repository 68. A pattern search is executable in response to occurrence of events of the types previously described or upon detection of a change in particular data (receipt of a specific diagnosis, for example) or in response to expiration of a particular time period.

The systems, processes and user interface display formats presented in FIGS. 1-17 are not exclusive. Other systems, processes and user interface forms may be derived in accordance with the principles of the invention to accomplish the same objectives. The inventive principles are applicable to streamlining and automating an event driven revenue management process in any industry or field. The principles are particularly applicable to the insurance, government and healthcare industries.

What is claimed is:

1. A system for processing claim data related to patient healthcare in response to clinical events, comprising:
   an interface processor for receiving messages identifying clinical events related to corresponding claim data elements concerning a patient;
   a source of rules for validating claim data elements concerning provision of individual services to a patient;
   a rules processor for automatically initiating application of a plurality of rules derived from said rules source to identify claim data element deficiencies and automatically correcting claim data element deficiencies to make a claim for reimbursement valid for payment by a payer organization in response to receiving said messages identifying said clinical events; and
   a result processor for automatically initiating performance of an action in response to a result derived by said application of said rules to individually validate different claim data elements.

2. A system according to claim 1, wherein
   said plurality of rules are automatically selected from said rules source in response to an identified type of said clinical event.

3. A system, for processing financial data related to patient healthcare in response to clinical events, comprising:
   an interface processor for receiving a message identifying a clinical event and a related change in healthcare data concerning a patient;
   a source of rules for determining characteristics associated with reimbursement for provision of an individual service to a patient;
   a rules processor for automatically initiating application of a plurality of rules automatically selected from said rules source in response to an identified type of said clinical event to process financial data concerning provision of a plurality of individual services to said patient to validate a claim for reimbursement for performance of said services is valid for payment by a payer organization in response to receiving said message identifying said clinical event; and
   a result processor for automatically initiating performance of an action in response to a result derived by said application of said rule to process said financial data wherein
   said action comprises automatic correction of claim data deficiencies to make said claim for reimbursement valid for payment by said payer organization and
   said clinical event comprises at least one of, (a) generation of an indication of occurrence of provision of healthcare to a patient by an operating process, (b) generation of an indication of occurrence of provision of healthcare to a patient by patient monitoring equipment and (c) generation of an indication of occurrence of provision of healthcare to a patient by a medical device.

4. A system for processing financial data related to patient healthcare in response to clinical events, comprising:
   an interface processor for receiving a message identifying a clinical event and a related change in healthcare data concerning a patient;
   a source of rules for determining characteristics associated with reimbursement for provision of an individual service to a patient;

a rules processor for automatically initiating application of a plurality of rules automatically selected from said rules source in response to an identified type of said clinical event to process financial data concerning provision of a plurality of individual services to said patient to validate a claim for reimbursement for performance of said services is valid for payment by a payer organization in response to receiving said message identifying said clinical event; and a result processor for automatically initiating performance of an action in response to a result derived by said application of said rule to process said financial data wherein said result processor, in response to said derived result, initiates addition of a task to a worklist of a healthcare worker, said task comprising review of data derived as said result of said application of said rule to process said financial data and said result processor provides data prompting a user with a candidate alternative service and said data for review comprises at least one of, (a) a notification of denial of a particular treatment for a patient, (b) a notification of a requirement for a waiver to be provided for qualification of a treatment for reimbursement and (c) a result of processing a trial claim for reimbursement for a particular treatment for a patient.

5. A system for processing financial data related to patient healthcare in response to clinical events, comprising:

an interface processor for receiving a message identifying a clinical event and a related change in healthcare data concerning a patient;

a source of rules for determining characteristics associated with reimbursement for provision of an individual service to a patient;

a rules processor for automatically initiating application of a plurality of rules automatically selected from said rules source in response to an identified type of said clinical event to process financial data concerning provision of a plurality of individual services to said patient to validate a claim for reimbursement for performance of said services is valid for payment by a payer organization in response to receiving said message identifying said clinical event; and a result processor for automatically initiating performance of an action in response to a result derived by said application of said rule to process said financial data wherein said result processor, in response to said derived result, initiates addition of a task to a worklist of a healthcare worker, said task comprising review of data derived as said result of said application of said rule to process said financial data and wherein said rules processor automatically initiates application of rules derived from said rules source to process data concerning provision of individual services to said patient by examining a billing record to determine if no payment has been made by a healthcare payer organization within a predetermined period in response to receiving said message identifying said clinical event, and said result processor, in response to said derived result, automatically initiates actions to collect said overdue payment.

6. A system for processing financial data related to patient healthcare in response to clinical events, comprising:

an interface processor for receiving a message identifying a clinical event and a related change in healthcare data concerning a patient;

a source of rules for determining characteristics associated with reimbursement for provision of an individual service to a patient;

a rules processor for automatically initiating application of a plurality of rules automatically selected from said rules source in response to an identified type of said clinical event to process financial data concerning provision of a plurality of individual services to said patient to validate a claim for reimbursement for performance of said services is valid for payment by a payer organization in response to receiving said message identifying said clinical event; and a result processor for automatically initiating performance of an action in response to a result derived by said application of said rule to process said financial data wherein said result processor, in response to said derived result, initiates addition of a task to a worklist of a healthcare worker, said task comprising review of data derived as said result of said application of said rule to process said financial data and wherein said result processor, in response to said derived result, initiates addition of a task to a worklist for medical equipment.

7. A system for processing financial data related to patient healthcare in response to clinical events, comprising:

an interface processor for receiving a message identifying a clinical event and a related change in healthcare data concerning a patient;

a source of rules for determining characteristics associated with reimbursement for provision of an individual service to a patient;

a rules processor for automatically initiating application of a plurality of rules automatically selected from said rules source in response to an identified type of said clinical event to process financial data concerning provision of a plurality of individual services to said patient to validate a claim for reimbursement for performance of said services is valid for payment by a payer organization in response to receiving said message identifying said clinical event; and a result processor for automatically initiating performance of an action in response to a result derived by said application of said rule to process said financial data wherein said result processor, in response to said derived result, initiates addition of a task to a worklist of a healthcare worker, said task comprising review of data derived as said result of said application of said rule to process said financial data and wherein said result processor automatically initiates a search for records of services not billed for and said characteristics associated with reimbursement to a provider for provision of an individual service to a patient, comprise at least one of, (a) an expected reimbursement amount for provision of an individual service to a patient, (b) an effective benefit period for said reimbursement, (c) contract constraints for said reimbursement, (d) an indication said provision of said individual service to said patient qualifies for reimbursement under a particular insurance plan and (e) an indication said provision of said individual service to said patient is linked to provision of other services to said patient.

8. A system for processing claim data related to patient healthcare in response to clinical events, comprising:

an interface processor for receiving messages identifying clinical events related to corresponding claim data elements concerning a patient;

a source of rules for validating claim data elements concerning provision of individual services to a patient;

a rules processor for automatically initiating application of a plurality of rules automatically selected from said rules source in response to an identified type of said clinical event to individually validate different claim data elements concerning provision of corresponding different individual services to a patient are valid for reimbursement for payment by a payer organization in response to receiving said messages identifying said clinical events; and a result processor for automatically initiating performance of an action including initiating transfer of patient insurance and demographic data to a location accessible by a physician in response to a result derived by said application of said rules to individually validate different claim data elements wherein said action comprises automatic correction of claim data deficiencies to make said claim for reimbursement valid for payment by said payer organization and said rules processor collates validated claim data elements to produce a claim for provision of a plurality of services to said patient.

9. A system according to claim 8, wherein said rules processor validates a plurality of claim data elements comply with reimbursement rules requiring combined reimbursement for provision of different services.

10. A system according to claim 8, wherein said rules processor automatically initiates submission of said validated collated claim data elements to a payer, in response to successful validation.

11. A system for processing claim data related to patient healthcare in response to clinical events, comprising:

an interface processor for receiving messages identifying clinical events related to corresponding claim data elements concerning a patient;

a source of rules for validating claim data elements concerning provision of individual services to a patient;

a rules processor for automatically initiating application of a plurality of rules automatically selected from said rules source in response to an identified type of said clinical event to individually validate different claim data elements concerning provision of corresponding different individual services to a patient are valid for reimbursement for payment by a payer organization in response to receiving said messages identifying said clinical events; and a result processor for automatically initiating performance of an action including initiating transfer of patient insurance and demographic data to a location accessible by a physician in response to a result derived by said application of said rules to individually validate different claim data elements wherein said result processor prompts a user with a candidate alternative service in response to unsuccessful validation of a claim data element for provision of a particular service.

* * * * *